(12) United States Patent
Peterson

(10) Patent No.: US 10,179,007 B2
(45) Date of Patent: Jan. 15, 2019

(54) REINFORCING SLIDER FOR SURGICAL HAND TOOL

(71) Applicant: Medical Instrument Development Laboratories, Inc., San Leandro, CA (US)

(72) Inventor: Erik William Peterson, Walnut Creek, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 541 days.

(21) Appl. No.: 14/811,020

(22) Filed: Jul. 28, 2015

(65) Prior Publication Data

US 2016/0022256 A1    Jan. 28, 2016

Related U.S. Application Data

(60) Provisional application No. 62/029,848, filed on Jul. 28, 2014.

(51) Int. Cl.
| | |
|---|---|
| *A61B 1/32* | (2006.01) |
| *A61B 17/34* | (2006.01) |
| *A61F 9/007* | (2006.01) |
| *A61B 17/00* | (2006.01) |

(52) U.S. Cl.
CPC .......... *A61B 17/3423* (2013.01); *A61F 9/007* (2013.01); *A61F 9/00763* (2013.01); *A61B 2017/00544* (2013.01)

(58) Field of Classification Search
CPC combination set(s) only.
See application file for complete search history.

(56) References Cited

U.S. PATENT DOCUMENTS

| | | | |
|---|---|---|---|
| 3,659,607 A | 5/1972 | Banko | |
| 4,795,432 A | 1/1989 | Karczmer | |
| 4,932,940 A * | 6/1990 | Walker | ............... A61M 5/3271 |
| | | | 604/110 |
| 6,013,046 A | 1/2000 | Maaskamp et al. | |
| (Continued) | | | |

FOREIGN PATENT DOCUMENTS

| | | |
|---|---|---|
| WO | 2007035621 | 3/2007 |
| WO | 2014027268 | 2/2014 |

OTHER PUBLICATIONS

International Search Report for Application No. PCT/US15/42423 dated Dec. 29, 2015 (12 pages).

(Continued)

*Primary Examiner* — Sameh Boles
(74) *Attorney, Agent, or Firm* — Michael Best & Friedrich LLP

(57) ABSTRACT

A surgical hand tool includes a handle that has an inner cavity. The handle has a proximal end and a distal end. The surgical hand tool also includes a primary tube extending outwardly from the cavity at the distal end, a reinforcing slider slidably disposed over the primary tube, and a biasing member coupled to the handle that biases the reinforcing slider away from the handle. The surgical hand tool also includes a retention mechanism coupled to the handle, the retention mechanism configured to engage and disengage with the reinforcing slider to control relative movement between the reinforcement slider and the handle.

11 Claims, 4 Drawing Sheets

(56) References Cited

U.S. PATENT DOCUMENTS

| | | | |
|---|---|---|---|
| 6,159,185 | A | 12/2000 | Tanihata |
| 6,468,249 | B1 | 10/2002 | Steyn |
| 7,604,647 | B2 | 10/2009 | Chen |
| 8,419,549 | B2 | 7/2013 | Conston et al. |
| 8,608,753 | B2 * | 12/2013 | Luloh ................. A61F 9/00763 606/107 |
| 2008/0195135 | A1 | 8/2008 | Attinger |
| 2012/0271272 | A1 | 10/2012 | Hammack et al. |
| 2013/0053759 | A1 | 2/2013 | McCawley |
| 2013/0310751 | A1 | 11/2013 | Davis et al. |

OTHER PUBLICATIONS

International Written Opinion for Application No. PCT/US15/42423 dated Dec. 29, 2015 (9 pages).
Extended European Search Report for Application No. 15826438.2 dated Feb. 6, 2018 (6 pages).

* cited by examiner

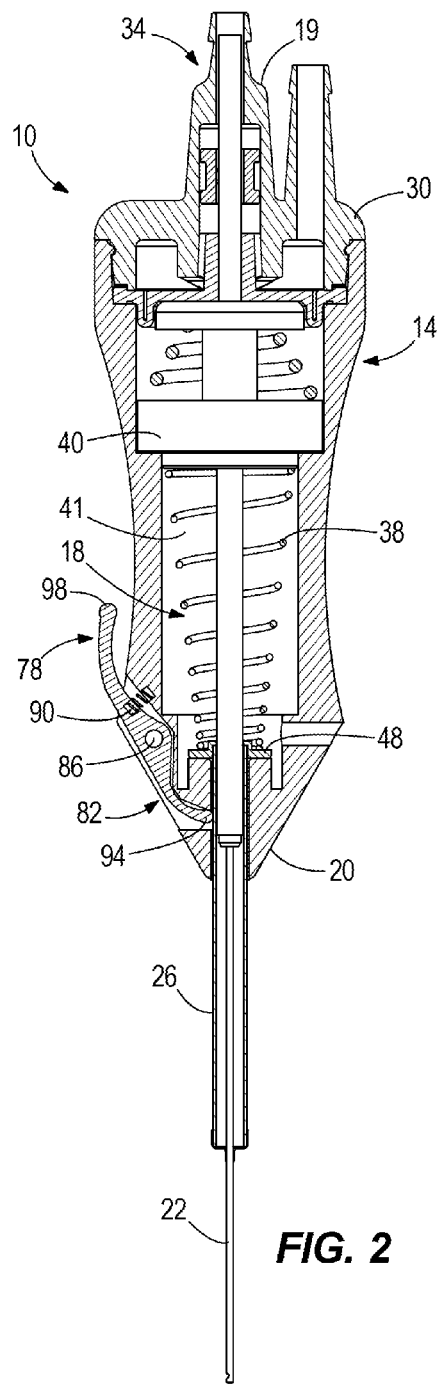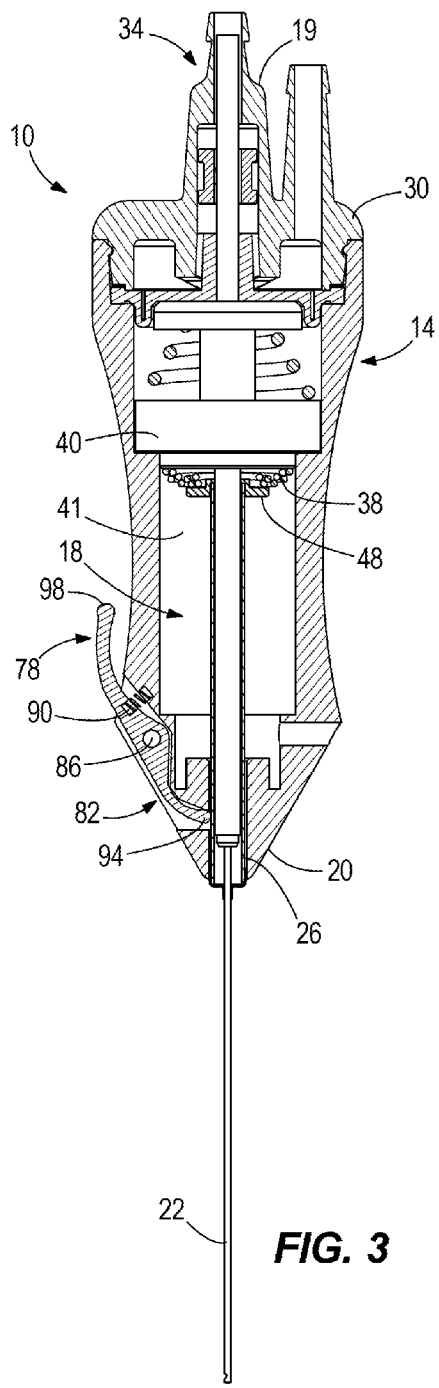

REINFORCING SLIDER FOR SURGICAL HAND TOOL

CROSS-REFERENCE TO RELATED APPLICATIONS

This application claims priority to U.S. Provisional Application No. 62/029,848, filed Jul. 28, 2014, the entire contents of which are incorporated herein by reference.

FIELD OF THE INVENTION

The present invention relates to surgical hand tools for ophthalmic surgery. More particularly, embodiments of the invention relate to reinforcement of small gauge needles used in surgical hand tools.

BACKGROUND

Many surgical instruments used in the posterior portion of an eye (e.g., a human eye) take the form of a thin tube or needle attached to a handle. The needle may be manufactured from, for example, stainless-steel hypodermic tubing. The tube passes through the wall of the eye and into the interior of the eye, while the handle is used by the surgeon to manipulate the tube from outside of the eye. A variety of tools, fluid, or optical conduits, etc., pass through the tube in order to perform some surgical function at the tip of the tube. Such instruments include, but are not limited to, aspirating cutters, scissors, forceps, fiber-optic illuminators and fiber-optic laser delivery devices. The tube is typically of 20, 23, 25 or 27 gauge (i.e., hypodermic needle gauge). The trend is to use smaller and smaller (i.e., larger gauge number) tubing as current technology evolves to miniaturize the functional elements of the instrument.

Typically, two such instruments are in use at any given time, one in either hand of the surgeon. Often times, one instrument provides illumination through an optical fiber while the other instrument performs some tissue cutting or manipulation function. In addition to using the instrument handles to position the tips of the instruments within the eye, it is common for the instrument handles to be used to "steer" the eye by rotating the eye within the eye socket so as to position a portion of interest of the eye into the field of view of a surgical microscope. This is possible because the points where the instrument tubes pass through the wall of the eye provide a means of applying force (i.e., rotating force) to the eye.

The practice of steering the eye with the instrument handles evolved in a period when most instruments used relatively robust 20 gauge tubing, which is approximately 0.9 mm in diameter. With modern instruments being as small as 27 gauge, which is approximately 0.4 mm in diameter, the practice of steering the eye frequently results in damage to the instrument.

Paralleling the trend to smaller tube diameters, there is also now a trend to place a cannula, a short section of hard tubing, usually with a larger external hub, into the incision through the wall of the eye. However, this practice further increases the likelihood of damage to the instrument, because the forces used by the surgeon to steer the eye are then concentrated at the point where the instrument tube enters the hard cannula. In contrast, steering forces are more evenly distributed on the instrument when the instrument is directly coupled to the softer tissues of the eye wall.

SUMMARY

In accordance with one construction, a surgical hand tool includes a handle that has an inner cavity. The handle has a proximal end and a distal end. The surgical hand tool also includes a primary tube that extends outwardly from the cavity at the distal end, a reinforcing slider slidably disposed over the primary tube, and a biasing member coupled to the handle that biases the reinforcing slider away from the handle. The surgical hand tool also includes a retention mechanism coupled to the handle. The retention mechanism is configured to engage and disengage with the reinforcing slider to control relative movement between the reinforcement slider and the handle.

In accordance with another construction, a surgical hand tool includes a handle that has an inner cavity. The handle has a proximal end and a distal end. The surgical hand tool also includes a primary tube extending outwardly from the cavity at the distal end, a reinforcing slider slidably disposed over the primary tube, and a biasing member coupled to the handle that biases the reinforcing slider away from the handle, wherein the biasing member includes an elastomeric end piece made of a resilient material that is coupled to the distal end of the handle.

In accordance with another construction, a method for using a surgical hand tool includes grasping a handle of the surgical hand tool. The handle has an inner cavity and a proximal end and a distal end. A primary tube extends from the distal end and a reinforcing slider is slidably coupled over the primary tube. The method also includes moving the handle forward until the reinforcing slider causes a biasing member to compress, temporarily fixing the reinforcing slider relative to the handle with a retention mechanism, and after temporarily fixing the reinforcing slider relative to the handle, releasing the reinforcing slider to allow the reinforcing slider to move relative to the handle.

Other aspects of the invention will become apparent by consideration of the detailed description and accompanying drawings.

BRIEF DESCRIPTION OF THE DRAWINGS

FIG. 2 is a side cross-sectional view of the hand tool of FIG. 1, illustrating the reinforcing slider in an extended position.

FIG. 3 is a side cross-sectional view of the hand tool of FIG. 1, illustrating the reinforcing slider in a retracted position.

Figure 1:
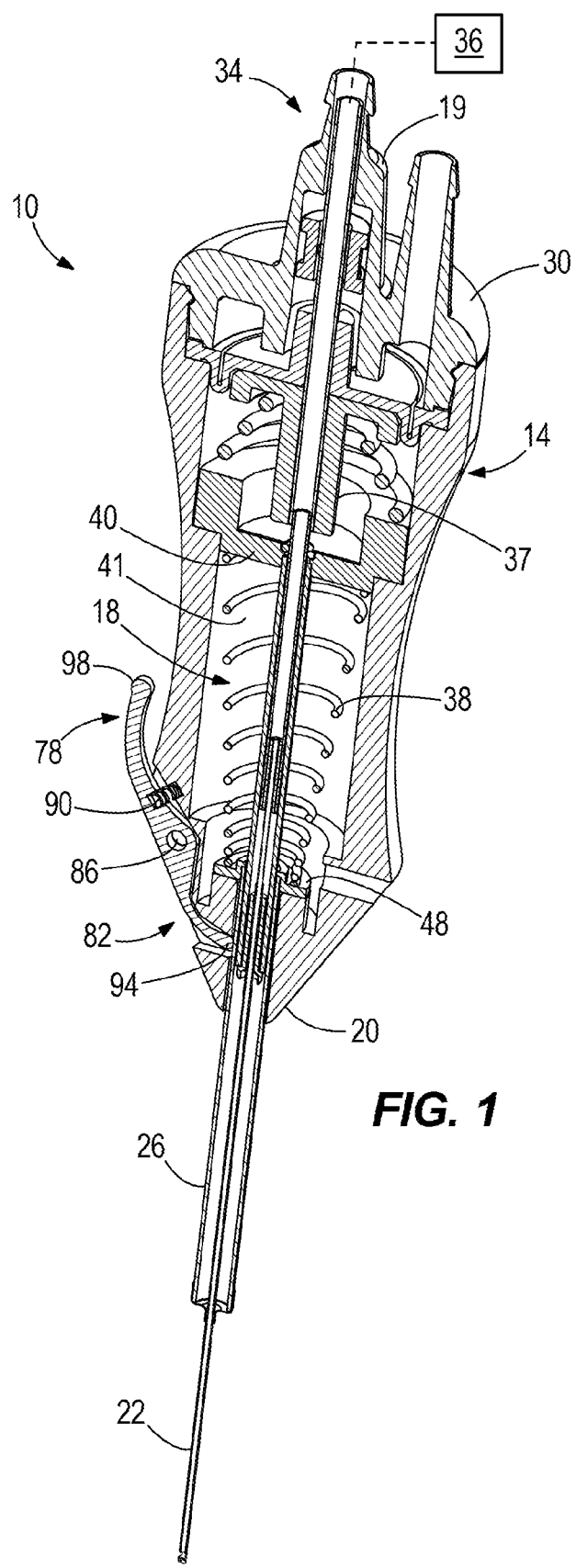
FIG. 1 is a perspective cross-sectional view of a hand tool including a reinforcing slider in accordance with one construction.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION

FIGS. 1-5 illustrate a hand tool 10 in accordance with one construction. The hand tool 10 includes a handle 14. The handle 14 has an inner cavity 18 and has a proximal end 19 and a distal end 20. In the illustrated construction, the handle 14 has a contoured shape such that a user is able to grip or grasp an outside of the handle 14 comfortably.

The hand tool 10 also includes a primary tube 22 (e.g., a needle) extending outwardly from the inner cavity 18 at the distal end 20, a reinforcing slider 26 (e.g., a secondary outer tube) slidably disposed over the primary tube 22, and an end cap 30 that encloses the inner cavity 18 at the proximal end 19 of the handle 14.

As illustrated in FIGS. 1-4, in some constructions the end cap 30 includes one or more attachment features 34 (e.g., an air inlet) engageable by an actuation system 36 (e.g., a pneumatic driver, illustrated schematically in FIG. 1) to facilitate a surgical function (e.g., cutting, illumination, suction, etc.). For example, in some constructions, the primary tube 22 is coupled to an internal mechanism 37 to perform one or more of the various possible surgical functions (e.g., cutting, illumination, suction, etc.). In the illustrated construction, the attachment feature 34 includes a suction outlet (at the center) and an air inlet (at the side). The internal mechanism 37 is driven by pulses of air pressure applied at the air inlet and is coupled to a cutting device at the distal end of primary tube 22. The suction outlet is also coupled to the cutting device to facilitate removal of the cut material trough the primary tube 22. In other constructions, an optical fiber is disposed through the attachment feature 34 to deliver illumination at the distal end of primary tube 22. Other constructions include other types of attachment features 34 and/or internal mechanisms 37.

With continued reference to FIG. 1, in the illustrated construction the primary tube 22 is positioned at least partially within the inner cavity 18, with a portion extending outwardly from the distal end 20 of the handle 14. In some constructions, the primary tube 22 is relatively small in diameter (i.e., has a large gauge) to minimize the invasive nature of any surgical procedure to be performed with the hand tool 10. As such, the reinforcing slider 26 is used to provide extra structural support at the distal end 20 of the handle 14. In some constructions, the primary tube 22 is at least 20 gauge. In some constructions, the primary tube 22 is at least 23 gauge. In some constructions, the primary tube 22 is at least 25 gauge. In some constructions, the primary tube 22 is at least 27 gauge. Other constructions include different values and ranges.

With reference to FIGS. 2 and 3, in the illustrated construction, the reinforcing slider 26 is a tube that has a larger diameter than the primary tube 22. The reinforcing slider 26 is slidable between an extended position (FIG. 2), in which the reinforcing slider 26 covers a portion of the primary tube 22 such that only a relatively short length of the primary tube 22 extends past the reinforcing slider 26, and a retracted position (FIG. 3), in which the reinforcing slider 26 exposes a relatively longer length of the primary tube 22. As illustrated in FIGS. 2 and 3, while moving between the two positions the reinforcing slider 26 is at least partially received within the inner cavity 18 of the handle 14.

The hand tool 10 also includes a biasing member 38 that is coupled to the handle 14 and biases the reinforcing slider 26 toward the extended position and away from the handle 14. In the illustrated construction, the biasing member 38 is a compression spring disposed with the inner cavity 18, and is coupled to an inner attachment plate 40 at a first end of the biasing member 38. In some constructions, the inner attachment plate 40 is engaged with an inner side wall 41 of the inner cavity 18. In the illustrated construction, the biasing member 38 is also coupled to a disc 48 at a second, opposite end of the biasing member 38. The disc 48 is coupled to (e.g., integrally formed in one piece with) the reinforcing slider 26. The biasing force of the biasing member 38 forces the reinforcing slider 26 away from the attachment plate 40, and therefor into the extended position (FIG. 2).

Figure 4:
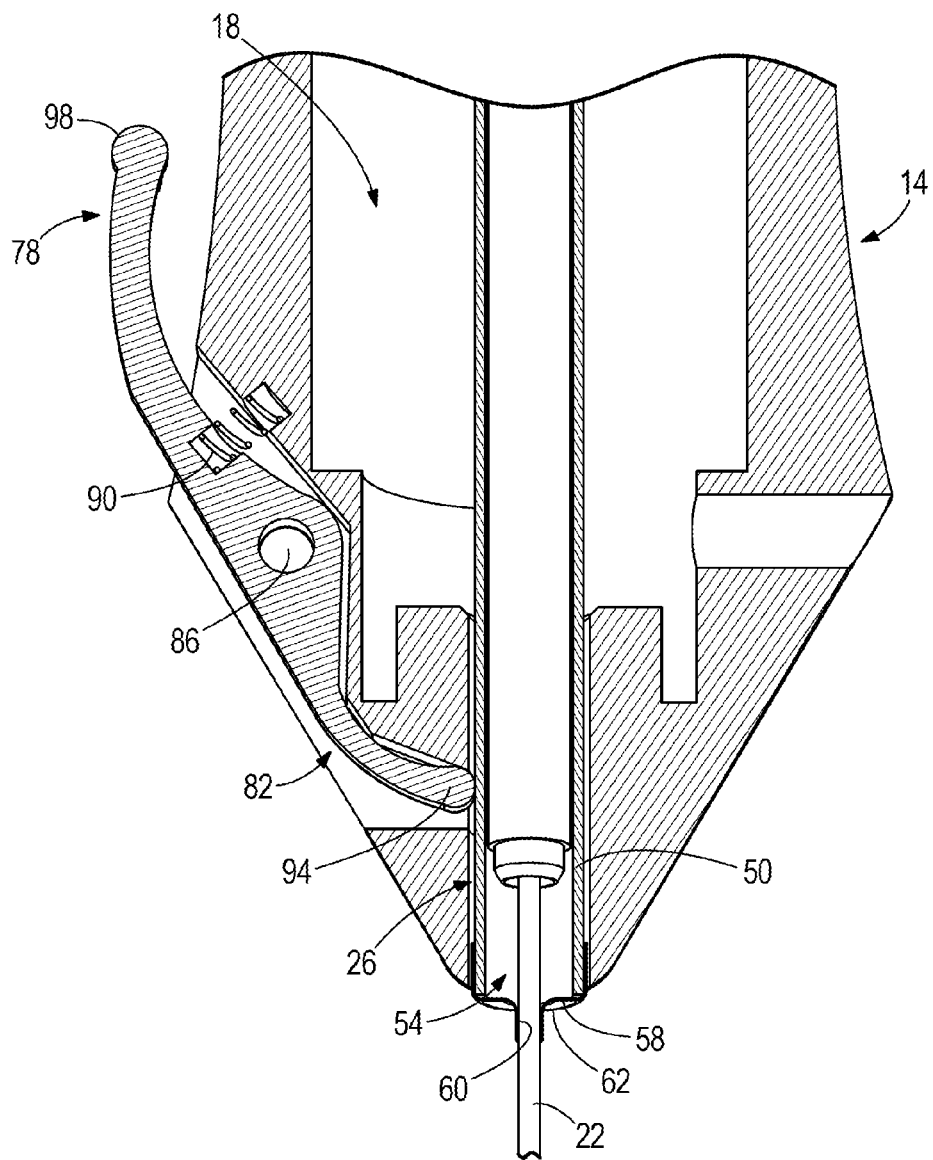
FIG. 4 is a cross-sectional view of a portion of the hand tool of FIG. 1, illustrating a distal end of the handle.

With reference to FIG. 4, the reinforcing slider 26 includes a tubular body 50 that has a hollow center 54 large enough to receive the primary tube 22 and any other components a surgeon may wish to use. The reinforcing slider 26 also includes a slider end cap 58, which encloses the hollow center 54, defines a distal end of the reinforcing slider 26, and includes an opening 60 through which the primary tube 22 passes.

Figures 5A, 5B, 5C:
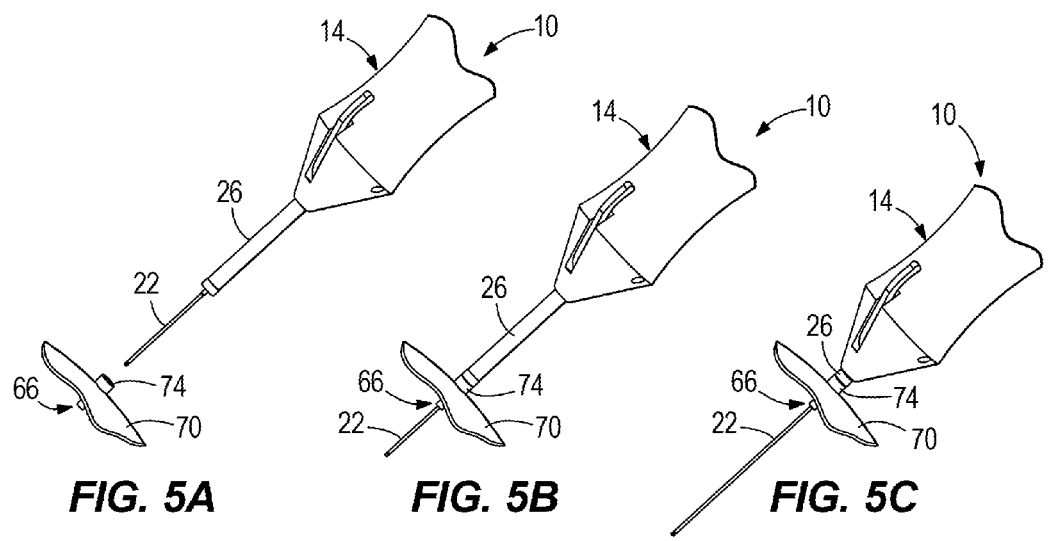
FIGS. 5A-C are a plurality of side views of a portion of a hand tool of FIG. 1, illustrating the reinforcing slider moving between the extended and retracted positions and engaging a cannula positioned in a wall of an eye.

At least a portion of the reinforcing slider 26 (e.g., the slider end cap 58) includes an engagement surface 62 that is configured to engage with a cannula or other object and cause movement of the reinforcing slider 26 toward the proximal end 19 of the handle 14, thereby overcoming the biasing force of the biasing member 38. For example, and with reference to FIGS. 5A-C, in some constructions a cannula 66 is provided during surgery. The cannula 66 is inserted into the incision in a wall of an eye 70. The cannula 66 includes a hub 74 that receives the primary tube 22. When the handle 14 is moved toward the cannula 66 (FIGS. 5A and 5B), the reinforcing slider 26 engages the hub 74 (FIG. 5B), and the reinforcing slider 26 is pushed inwardly by the cannula 66 with a force that overcomes the biasing force of the biasing member 38 (i.e., causing the biasing member 38 to compress), such that the reinforcing slider 26 is pressed into and received at least partially within the inner cavity 18 and moved into the retracted position (FIG. 5C).

As discussed above, it is common for instrument handles to be used to "steer" the eye by rotating the eye within the eye socket to position a portion of interest of the eye into the field of view of a surgical microscope. In some constructions, the reinforcing slider 26 absorbs at least some of these steering forces, thus reducing the steering forces applied to the primary tube 22. For example, as described above, as the handle 14 is moved toward the cannula 66, the reinforcing slider 26 eventually engages the hub 74. When the reinforcing slider 26 engages the hub 74, the reinforcing slider 26 and the hub 74 become at least temporarily coupled (e.g., via friction), so that a portion or all of the steering force required to push the hub 74 (and consequently rotate the eye 70) is transmitted to the reinforcing slider 26, and less force is transmitted to the primary tube 22. In some constructions the reinforcing slider 26 and/or the hub 74 include one or more additional features or structures that facilitate a releasable coupling between the reinforcing slider 26 and the hub 74.

With reference to FIGS. 1-4, the hand tool 10 also includes a retention mechanism 78. The retention mechanism 78 releasably engages and disengages the reinforcing slider 26 to hold the reinforcing slider 26 in place relative to the handle 14.

In the illustrated construction, the retention mechanism 78 includes an arm 82 that pivots on a pin 86 coupled to the handle 14. A biasing member 90 (e.g., a compression spring) biases the arm 82 to a position in which a first end 94 of the arm 82 engages the reinforcing slider 26 (e.g., via friction).

In some constructions the first end 94 and/or the reinforcing slider 26 include additional features (e.g., protrusions, bumps, etc.) to ensure positive engagement between the first end 94 and the reinforcing slider 26. When the retention mechanism 78 is engaged with the reinforcing slider 26, the force exerted by the biasing member 90 on the reinforcing slider 26 is transmitted through the arm 82 to the pin 86, and hence to the handle 14.

The arm 82 also has an opposite, second end 98. Applying a force on this second end 98, directed toward the handle 14, acts to compress the biasing member 90 and rotate the arm 82 such that the first end 94 disengages from the reinforcing slider 26. In the illustrated construction, for example, a surgeon can conveniently apply such a force to the second end 98 with a forefinger while continuing to grasp the handle 14 between a thumb and the other fingers.

Without the retention mechanism 78, a surgeon must maintain a force on the handle 14 sufficient to keep the biasing member 38 in a compressed state in order to cause the reinforcing slider 26 to retract from the extended position and expose a greater length of the primary tube 22 within the eye 70. This may lead to fatigue or make it more difficult for the surgeon to accurately position the end of the primary tube 22 within the eye 70. The retention mechanism 78 alleviates this burden. In particular, when the retention mechanism 78 is engaged with the reinforcing slider 26, the reinforcing slider 26 is retained and held in place relative to the handle 14, without the need to continuously apply force through the handle 14. When the surgeon is ready to move the primary tube 22 farther into the eye 70, the surgeon may then simply press on the opposite, second end 98, thereby releasing the engagement, and allowing the reinforcing slider 26 to retract farther into the handle 14. Other constructions include other types of retention mechanisms 78 than that illustrated, including retention mechanisms that do not use a biasing mechanism (e.g., retention mechanisms that instead rely on manual movement of the retention mechanism 78 into engagement with the reinforcing slider 26).

Figures 6A, 6B:
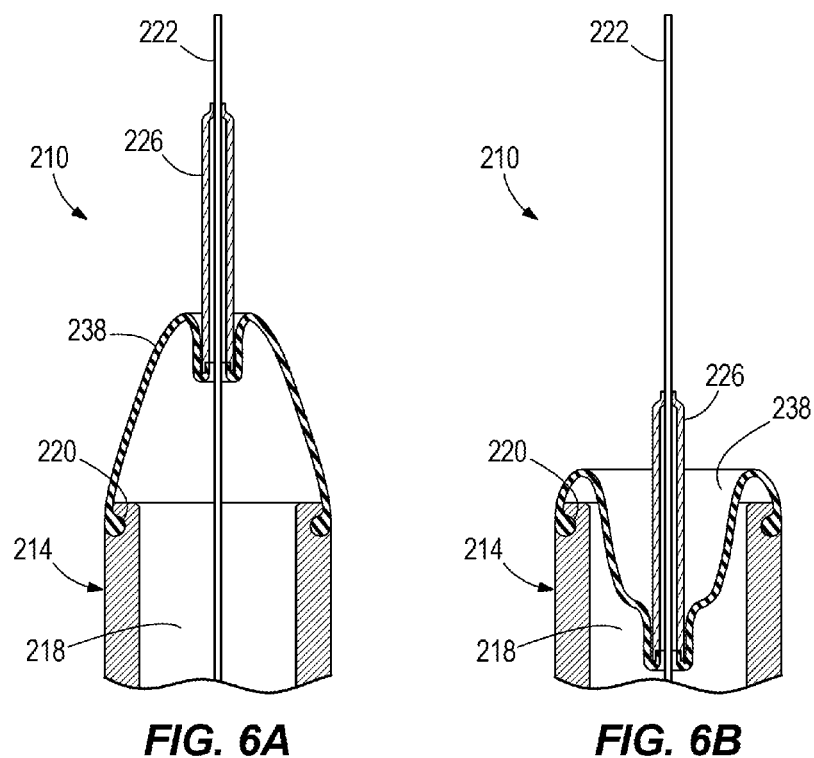
FIGS. 6A and 6B are cross-sectional views of a portion of a hand tool according to another construction, illustrating a reinforcing slider moving between an extended and a retracted position.

FIGS. 6A and 6B illustrate another construction in the form of a hand tool 210. The hand tool 210 is similar to the hand tool 10, and includes a handle 214 that has an inner cavity 218. The handle 214 also has a distal end 220.

The hand tool 210 also includes a primary tube 222 (e.g., a needle) extending outwardly from the inner cavity 218 at the distal end 220, and a reinforcing slider 226 (e.g., a secondary outer tube) slidably disposed over the primary tube 222. In some constructions, the hand tool 210 also includes a retention mechanism to engage and hold the reinforcing slider 226, such as retention mechanism 78.

In contrast to using the spring biasing member 38 of the handle tool 10 illustrated in FIGS. 1-5, however, the hand tool 210 instead utilizes a biasing member 238 in the form of an elastomeric end piece made of a resilient material that serves the function of a spring while also being coupled to and/or covering the distal end 220 of the handle 214. The biasing member 238 extends away from the distal end 220 in a naturally biased state. As illustrated in FIGS. 6A and 6B, the reinforcing slider 226 is configured to engage and press against the biasing member 238 (e.g., when the reinforcing slider 226 contacts a cannula like cannula 66 in FIGS. 5A-C) thereby pressing at least a portion of the biasing member 238 inwardly toward the inner cavity 218 and into the cavity 218, against a biasing force of the biasing member 238. As the reinforcing slider 226 is initially pressed and moved against the biasing member 238, the reinforcing slider 226 is still outside of the inner cavity 218 (FIG. 6A). Because of the conical shape of the biasing member 238 illustrated in FIGS. 6A and 6B, the elastomeric end piece doubles over itself when pressed further, until the reinforcing slider 226 is at least partially inside of the inner cavity 218 (FIG. 6B). Thus, the reinforcing slider 226 travels and moves at least some distance or length while engaged with the biasing member 238 before ever entering the inner cavity 218. In some constructions, a length that must be accommodated inside of the inner cavity 218 for the reinforcing slider 226 to travel into the inner cavity 218 is only approximately half of a total travel distance of the reinforcing slider 226. Other constructions of hand tools include different types of biasing members than those illustrated in FIGS. 1-6, and different travel distances for sliders into the handle cavities.

Although the invention has been described in detail with reference to certain preferred embodiments, variations and modifications exist within the scope and spirit of one or more independent aspects of the inventions as described.

What is claimed is:

1. A surgical hand tool comprising:
   a handle having an inner cavity, a proximal end, and a distal end;
   a primary tube extending outwardly from the cavity at the distal end;
   a reinforcing slider slidably disposed over the primary tube;
   a biasing member coupled to the handle that biases the reinforcing slider away from the handle; and
   a retention mechanism coupled to the handle, a portion of the retention mechanism configured to physically engage and disengage with the reinforcing slider to control relative movement between the reinforcement slider and the handle.

2. The surgical hand tool of claim 1, wherein the retention mechanism includes a movable arm that engages and disengages with the reinforcing slider, wherein the retention mechanism includes a pin coupled the handle, and wherein the arm is pivotally coupled to the pin.

3. The surgical hand tool of claim 1, wherein the retention mechanism includes a movable arm that engages and disengages with the reinforcing slider, wherein the arm includes a first end that engages and disengages with the reinforcing slider, and a second end that is engaged and disengaged by a user's finger.

4. The surgical hand tool of claim 1, wherein the retention mechanism includes a movable arm that engages and disengages with the reinforcing slider, wherein the biasing member is a first biasing member, and wherein the retention mechanism includes a second biasing member that biases the arm into engagement with the reinforcing slider.

5. The surgical hand tool of claim 1, wherein the retention mechanism includes a movable arm that engages and disengages with the reinforcing slider, wherein the movable arm engages and holds the reinforcing slider via a frictional engagement with the reinforcing slider.

6. The surgical hand tool of claim 1, wherein the biasing member includes a compression spring disposed within the cavity.

7. The surgical hand tool of claim 6, wherein the reinforcing slider is coupled to a disc, wherein the disc is coupled to the biasing member at a first end of the biasing member, and wherein a second, opposite end of the biasing member is coupled to an inner attachment plate disposed within the handle.

8. The surgical hand tool of claim 1, wherein the primary tube is at least 27 gauge.

9. The surgical hand tool of claim 1, wherein at least a portion of the reinforcing slider is slidably disposed within the cavity.

10. The surgical hand tool of claim 1, wherein the reinforcing slider is slidable between an extended position relative to the handle and a retracted position relative to the handle, and wherein the biasing member is configured to bias the reinforcing slider away from the distal end of the handle toward the extended position.

11. The surgical hand tool of claim 1, wherein the retention mechanism is a separate element from the biasing member.

\* \* \* \* \*